United States Patent
Frey et al.

(10) Patent No.: US 6,451,008 B1
(45) Date of Patent: *Sep. 17, 2002

(54) LASER BEAM DELIVERY AND EYE TRACKING SYSTEM

(75) Inventors: Rudolph W. Frey; James H. Burkhalter; Gary P. Gray, all of Orlando; Neil Zepkin, Casselberry; George Richard Downes, Jr.; John E. McWhirter, both of Orlando, all of FL (US)

(73) Assignee: Alcon, Inc. (CH)

( * ) Notice: Subject to any disclaimer, the term of this patent is extended or adjusted under 35 U.S.C. 154(b) by 0 days.

This patent is subject to a terminal disclaimer.

(21) Appl. No.: 09/376,133

(22) Filed: Aug. 17, 1999

Related U.S. Application Data

(63) Continuation of application No. 08/232,615, filed on Apr. 25, 1994, now Pat. No. 5,980,513.

(51) Int. Cl.$^7$ ................................................ A61B 9/018
(52) U.S. Cl. ............................................. 606/10; 606/5
(58) Field of Search ..................... 606/2, 3–6, 10–13

(56) References Cited

U.S. PATENT DOCUMENTS

| | | |
|---|---|---|
| 3,712,716 A | 1/1973 | Cornsweet et al. |
| 4,069,823 A | 1/1978 | Isahov et al. |
| 4,438,765 A | 3/1984 | Wilinsky |
| 4,443,075 A | 4/1984 | Crane |

(List continued on next page.)

FOREIGN PATENT DOCUMENTS

| | | |
|---|---|---|
| DE | 24 50 095 A1 | 4/1976 |
| DE | 199 26 476 A1 | 12/2000 |
| EP | 0 151 869 A2 | 8/1985 |
| WO | WO85/01869 | 5/1985 |
| WO | 8706478 | 11/1987 |
| WO | WO92/21999 | 12/1992 |
| WO | WO93/16631 | 9/1993 |

OTHER PUBLICATIONS

Pulianto et al, High–Speed Photography of Excimer Laser Ablation of the Cornea, Arch Ophthalmol; vol. 105, Sep. 1987.

Gailitis et al, Solid State Ultraviolet Laser Ablation of the Cornea and Synthetic Collagen Lenticules, vol. 105, Sep. 1987, pp. 566–562.

*Primary Examiner*—David M. Shay
(74) *Attorney, Agent, or Firm*—Allen, Dyer,k Doppelt, Milbrath & Gilchrist, P.A.

(57) ABSTRACT

A surface treatment laser beam delivery and tracking system is provided. The laser generates laser light along a original beam path at an energy level suitable for treating (e.g., eroding) a surface. An optical translator shifts the original beam path onto a resulting beam path. An optical angle adjuster changes the angle of the resulting beam path relative to the original beam path such that the laser light is incident on, and spatially distributed, the surface to be treated. A motion sensor transmits light energy to the surface and receives reflected light energy from the surface via the optical angle adjuster. The light energy transmitted by the motion sensor travels on a path that is parallel to the shifted beam as they travel through the optical angle adjuster. The reflected light energy is used by the motion sensor to detect movement of the surface relative to the original beam path and generate error control signals indicative of the movement. The optical angle adjuster is responsive to the error control signals to change the angle of the resulting beam path and the angle of the motion sensor's light energy in correspondence with one another. In this way, the beam originating from the treatment laser and the light energy originating from the motion sensor track together with the surface movement.

44 Claims, 4 Drawing Sheets

U.S. PATENT DOCUMENTS

| | | |
|---|---|---|
| 4,579,430 A | 4/1986 | Bille |
| 4,669,466 A | 6/1987 | L'Esperance |
| 4,702,245 A | 10/1987 | Schroder et al. |
| 4,718,418 A | 1/1988 | L'Esperance, Jr. |
| 4,721,379 A | 1/1988 | L'Esperance |
| 4,729,372 A | 3/1988 | L'Esperance, Jr. |
| 4,759,615 A | 7/1988 | Bainbridge et al. |
| 4,848,340 A | 7/1989 | Bille et al. |
| 4,881,808 A | 11/1989 | Bille et al. |
| 4,901,718 A | 2/1990 | Bille et al. |
| 4,907,586 A * | 3/1990 | Bille et al. ............ 606/5 |
| 4,941,093 A | 7/1990 | Marshall et al. |
| 4,972,836 A | 11/1990 | Schenk |
| 5,048,946 A | 9/1991 | Sklar |
| 5,057,102 A | 10/1991 | Tonioka |
| 5,098,426 A * | 3/1992 | Sklar et al. ............ 606/5 |
| 5,178,617 A | 1/1993 | Kuizenya |
| 5,302,979 A | 4/1994 | Maeda et al. |
| 5,329,544 A | 7/1994 | Shachrai et al. |
| 5,331,131 A | 7/1994 | Opdyke |
| 5,345,281 A | 9/1994 | Toboada et al. |
| 5,350,374 A | 9/1994 | Smith |
| 5,410,376 A | 4/1995 | Cornsweet |
| 5,632,742 A * | 5/1997 | Frey et al. ............ 606/4 |
| 5,752,950 A * | 5/1998 | Frey et al. ............ 606/13 |
| 5,980,513 A | 11/1999 | Frey et al. |
| 5,993,441 A | 11/1999 | Muller et al. |
| 6,302,879 B1 * | 10/2001 | Frey et al. ............ 606/12 |

* cited by examiner

LASER BEAM DELIVERY AND EYE TRACKING SYSTEM

CROSS REFERENCE TO RELATED APPLICATION

This application is a continuation of Application Ser. No. 08/232,615, filed Apr. 25, 1994, U.S. Pat. No. 5,980,513 both of which are commonly owned and assigned with the present invention.

FIELD OF THE INVENTION

The invention relates generally to laser systems, and more particularly to a laser system used to erode a moving surface such as an eye's corneal tissue.

BACKGROUND OF THE INVENTION

Use of lasers to erode all or a portion of a workpiece's surface is known in the art. In the field of ophthalmic medicine, photorefractive keratectomy (PRK) is a procedure for laser correction of focusing deficiencies of the eye by modification of corneal curvature. PRK is distinct from the use of laser-based devices for more traditional ophthalmic surgical purposes, such as tissue cutting or thermal coagulation. PRK is generally accomplished by use of a 193 nanometer wavelength excimer laser beam that ablates away the workpiece, i.e., corneal tissue, in a photo decomposition process. Most clinical work to this point has been done with a laser operating at a fluence level of 120–195 mJ/cm$^2$ and a pulse-repetition rate of approximately 5–10 Hz. The procedure has been referred to as "corneal sculpting."

Before sculpting of the cornea takes place, the epithelium or outer layer of the cornea is mechanically removed to expose Bowman's membrane on the anterior surface of the stroma. At this point, laser ablation at Bowman's layer can begin. An excimer laser beam is preferred for this procedure. The beam may be variably masked during the ablation to remove corneal tissue to varying depths as necessary for recontouring the anterior stroma. Afterward, the epithelium rapidly regrows and resurfaces the contoured area, resulting in an optically correct (or much more nearly so) cornea. In some cases, a surface flap of the cornea is folded aside and the exposed surface of the cornea's stroma is ablated to the desired surface shape with the surface flap then being replaced.

Phototherapeutic keratectomy (PTK) is a procedure involving equipment functionally identical to the equipment required for PRK. The PTK procedure differs from PRK in that rather than reshaping the cornea, PTK uses the aforementioned excimer laser to treat pathological superficial corneal dystrophies, which might otherwise require corneal transplants.

In both of these procedures, surgical errors due to application of the treatment laser during unwanted eye movement can degrade the refractive outcome of the surgery. The eye movement or eye positioning is critical since the treatment laser is centered on the patient's theoretical visual axis which, practically speaking, is approximately the center of the patient's pupil. However, this visual axis is difficult to determine due in part to residual eye movement and involuntary eye movement known as saccadic eye movement. Saccadic eye movement is high-speed movement (i.e., of very short duration, 10–20 milliseconds, and typically up to 1° of eye rotation) inherent in human vision and is used to provide dynamic scene to the retina. Saccadic eye movement, while being small in amplitude, varies greatly from patient to patient due to psychological effects, body chemistry, surgical lighting conditions, etc. Thus, even though a surgeon may be able to recognize some eye movement and can typically inhibit/restart a treatment laser by operation of a manual switch, the surgeon's reaction time is not fast enough to move the treatment laser in correspondence with eye movement.

SUMMARY OF THE INVENTION

Accordingly, it is an object of the present invention to provide a laser beam delivery and eye tracking method and system that is used in conjunction with a laser system capable of eroding a surface.

Another object of the present invention is to provide a system for delivering a treatment laser to a surface and for automatically redirecting the treatment laser to compensate for movement of the surface.

Still another object of the present invention is to provide a system for delivering a corneal ablating laser beam to the surface of an eye in a specific pattern about the optical center of the eye, and for automatically redirecting the corneal ablating laser beam to compensate for eye movement such that the resulting ablating pattern is the same regardless of eye movement.

Yet another object of the present invention is to provide a laser beam delivery and eye tracking system for use with an ophthalmic treatment laser where the tracking operation detects eye movement in a non-intrusive fashion.

A further object of the present invention is to provide a laser beam delivery and eye tracking system for automatically delivering and maintaining a corneal ablating laser beam with respect to the geometric center of an eye's pupil or a doctor defined offset from the center of the eye's pupil. A special object of this invention is the use of the laser pulses which are distributed in a pattern of discrete ablations to shape objects other than for corneal ablating.

Other objects and advantages of the present invention will become more obvious hereinafter in the specification and drawings.

In accordance with the present invention, an eye treatment laser beam delivery and eye tracking system is provided. A treatment laser and its projection optics generate laser light along an original beam path (i.e., the optical axis of the system) at an energy level suitable for treating the eye. An optical translator shifts the original beam path in accordance with a specific scanning pattern so that the original beam is shifted onto a resulting beam path that is parallel to the original beam path. An optical angle adjuster changes the resulting beam path's angle relative to the original beam path such that the laser light is incident on the eye.

An eye movement sensor detects measurable amounts of movement of the eye relative to the system's optical axis and then generates error control signals indicative of the movement. The eye movement sensor includes: 1) a light source for generating light energy that is non-damaging with respect to the eye, 2) an optical delivery arrangement for delivering the light energy on a delivery light path to the optical angle adjuster in a parallel relationship with the resulting beam path of the treatment laser, and 3) an optical receiving arrangement. The parallel relationship between the eye movement sensor's delivery light path and the treatment laser's resulting beam path is maintained by the optical angle adjuster. In this way, the treatment laser light and the eye movement sensor's light energy are incident on the eye in their parallel relationship.

A portion of the eye movement sensor's light energy is reflected from the eye as reflected energy traveling on a reflected light path back through the optical angle adjuster. The optical receiving arrangement detects the reflected energy and generates the error control signals based on the reflected energy. The optical angle adjuster is responsive to the error control signals to change the treatment laser's resulting beam path and the eye movement sensor's delivery light path in correspondence with one another. In this way, the beam originating from the treatment laser and the light energy originating from the eye movement sensor track along with the eye's movement.

In carrying out this technique, the pattern constitutes overlapping but not coaxial locations for ablation to occur with each pulse removing a microvolume of material by ablation or erosion. For different depths, a pattern is repeated over those areas where increased ablation is needed. The laser pulses are usually at a certain pulse repetition rate. The subsequent pulses in a sequence are spaced at least one pulse beam width from the previous pulse and at a distance the ablated particles will not substantialy interfere with the subsequent pulse. In order to maximize the speed of the ablation, the subsequent pulse is spaced sufficiently close to enable the beam to be moved to the successive location within the time of the pulse repetition. The ablation is carried out on an object until a desired specific shape is achieved.

This technique is fundamentally new and may be used on objects other than corneas.

Patents entitled "Eye Movement Sensing Method and System," having Application Ser. No. 08/232,990, filed Apr. 25, 1994 and issuing as U.S. Pat. No. 5,632,742, and "Laser Sculpting System and Method," having Application Ser. No. 08/232,956, filed Apr. 25, 1994 and issuing as U.S. Pat. No. 5,849,006, include disclosure herein incorporated by reference as provided for in above-referenced related applications.

DETAILED DESCRIPTION OF THE INVENTION

Figure 1:
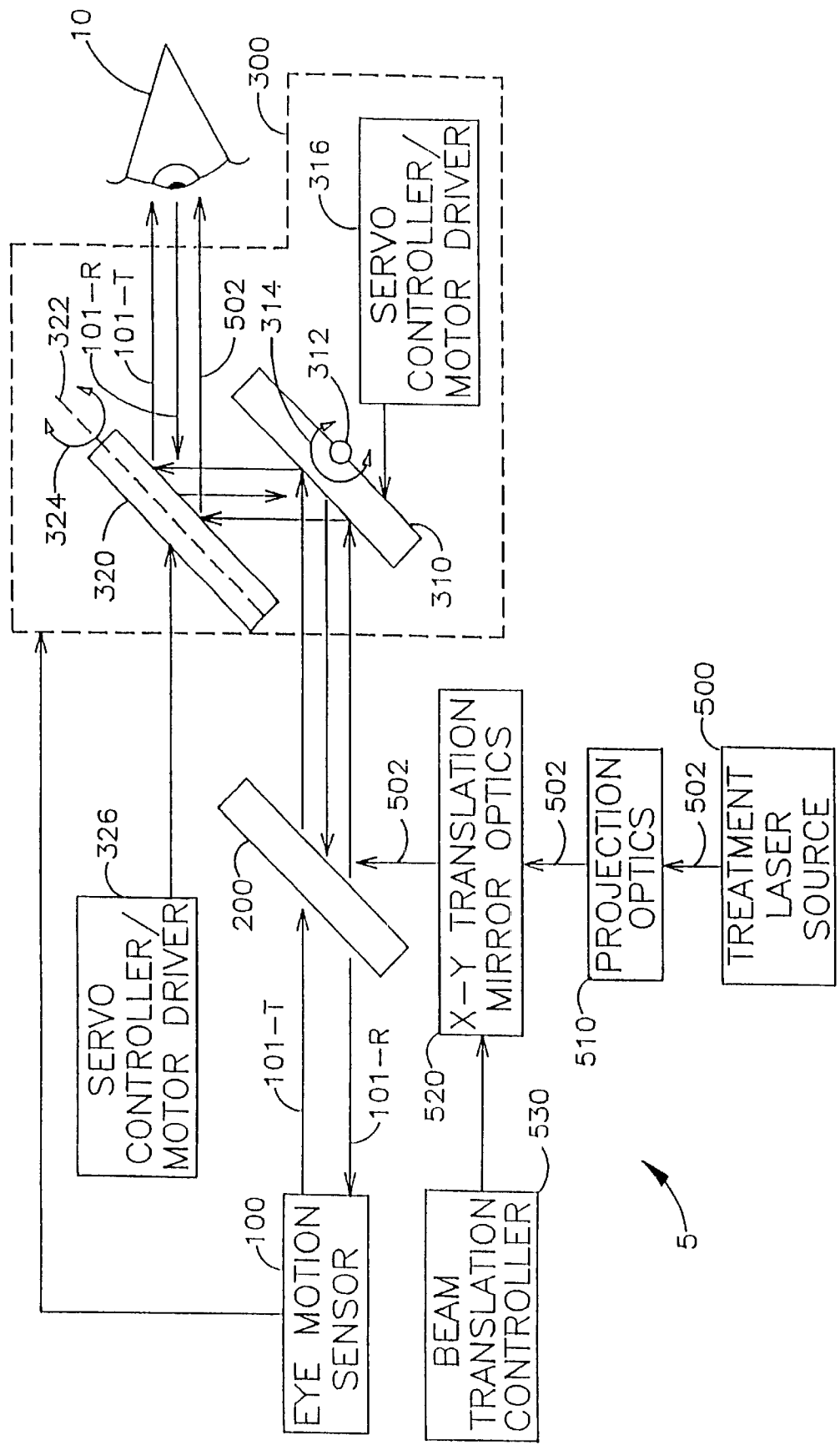
FIG. 1 is a block diagram of a laser beam delivery and eye tracking system in accordance with the present invention as it would be used in conjunction with an ophthalmic treatment laser.

Referring now to the drawings, and more particularly to FIG. 1, a block diagram is shown of a laser beam delivery and eye tracking system referenced generally by the numeral 5. The laser beam delivery portion of system 5 includes treatment laser source 500, projection optics 510, X-Y translation mirror optics 520, beam translation controller 530, dichroic beamsplitter 200, and beam angle adjustment mirror optics 300. By way of example, it will be assumed that treatment laser 500 is a 193 nanometer wavelength excimer laser used in an ophthalmic PRK (or PTK) procedure performed on a movable workpiece. e.g., eye 10. However, it is to be understood that the method and system of the present invention will apply equally as well to movable workpieces other than an eye, and further to other wavelength surface treatment or surface eroding lasers. The laser pulses are distributed as shots over the area to be ablated or eroded, preferably in a distributed sequence. A single laser pulse of sufficient power to cause ablation creates a micro cloud of ablated particles which interferes with the next laser pulse if located in the same or immediate point. To avoid this interference, the next laser pulse is spatially distributed to a next point of erosion or ablation that is located a sufficient distance so as to avoid the cloud of ablated particles. Once the cloud is dissipated, another laser pulse is made adjacent the area prior eroded so that after the pattern of shots is completed the cumulative shots fill in and complete said pattern so that the desired shape of the object or cornea is achieved.

Figure 2:
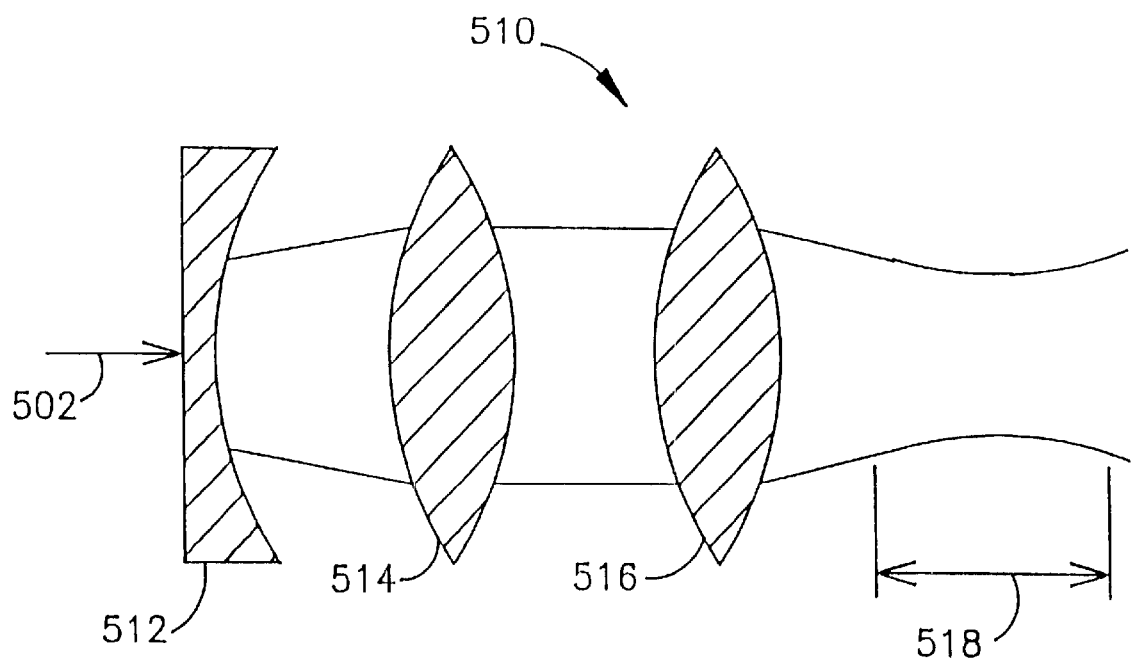
FIG. 2 is a sectional view of the projection optics used with the ophthalmic treatment laser embodiment of the laser beam delivery portion of the present invention.

In operation of the beam delivery portion of system 5, laser source 500 produces laser beam 502 which is incident upon projection optics 510. Projection optics 510 adjusts the diameter and distance to focus of beam 502 depending on the requirements of the particular procedure being performed. For the illustrative example of an excimer laser used in the PRK or PTK procedure, projection optics 510 includes planar concave lens 512, and fixed focus lenses 514 and 516 as shown in the sectional view of FIG. 2. Lenses 512 and 514 act together to form an afocal telescope that expands the diameter of beam 502. Fixed focus lens 516 focuses the expanded beam 502 at the workpiece, i.e., eye 10, and provides sufficient depth, indicated by arrow 518, in the plane of focus of lens 516. This provides flexibility in the placement of projection optics 510 relative to the surface of the workpiece. An alternative implementation is to eliminate lens 514 when less flexibility can be tolerated.

After exiting projection optics 510, beam 502 impinges on X-Y translation mirror optics 520 where beam 502 is translated or shifted independently along each of two orthogonal translation axes as governed by beam translation controller 530. Controller 530 is typically a processor programmed with a predetermined set of two-dimensional translations or shifts of beam 502 depending on the particular ophthalmic procedure being performed. For the illustrative example of the excimer laser used in a PRK or PTK procedure, controller 530 may be programmed in accordance with the aforementioned copending patent application entitled "Laser Sculpting System and Method". The programmed shifts of beam 502 are implemented by X-Y translation mirror optics 520.

Figure 3:
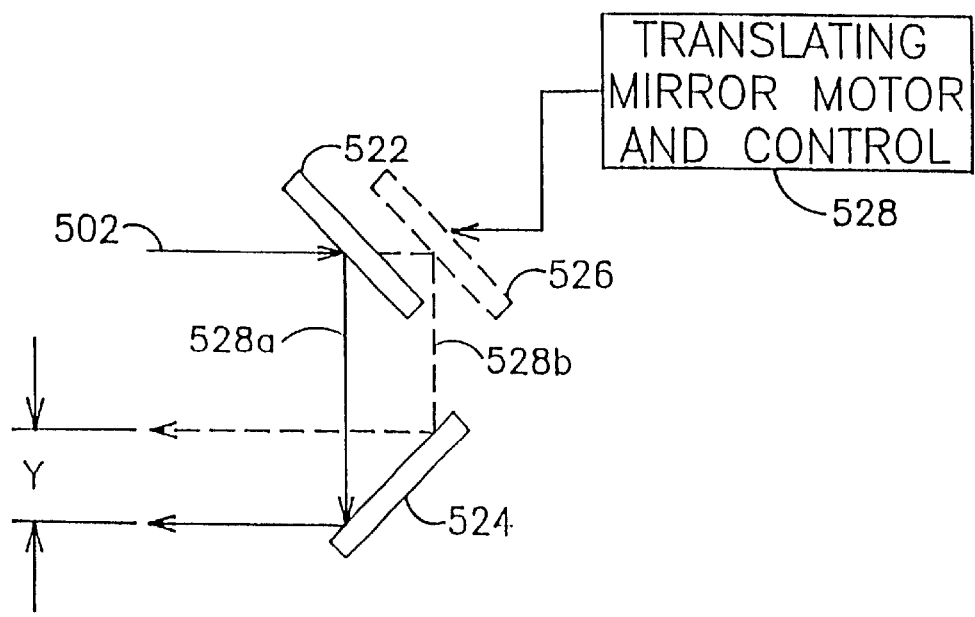
FIG. 3 illustrates diagrammatically an optical arrangement of mirrors used to produce translational shifts in a light beam along one axis.

Each X and Y axis of translation is independently controlled by a translating mirror. As shown diagrammatically in FIG. 3, the Y-translation operation of X-Y translation mirror optics 520 is implemented using translating mirror 522. Translating mirror 522 is movable between the position shown and the position indicated by dotted line 526. Movement of translating mirror 522 is such that the angle of the output beam with respect to the input beam remains constant. Such movement is brought about by translation mirror motor and control 525 driven by inputs received from beam translation controller 530. By way of example, motor and control 525 can be realized with a motor from Trilogy Systems Corporation (e.g., model T050) and a control board from Delta Tau Systems (e.g., model 400-602276 PMAC).

With translating mirror 522 positioned as shown, beam 502 travels the path traced by solid line 528a. With translating mirror 522 positioned along dotted line 526, beam 502 travels the path traced by dotted line 528b. A similar translating mirror (not shown) would be used for the X-translation operation. The X-translation operation is accomplished in the same fashion but is orthogonal to the Y-translation. The X-translation may be implemented prior or subsequent to the Y-translation operation.

The eye tracking portion of system 5 includes eye movement sensor 100, dichroic beamsplitter 200 and beam angle adjustment mirror optics 300. Sensor 100 determines the amount of eye movement and uses same to adjust mirrors 310 and 320 to track along with such eye movement. To do this, sensor 100 first transmits light energy 101-T which has been selected to transmit through dichroic beamsplitter 200. At the same time, after undergoing beam translation in accordance with the particular treatment procedure, beam 502 impinges on dichroic beamsplitter 200 which has been selected to reflect beam 502 (e.g., 193 nanometer wavelength laser beam) to beam angle adjustment mirror optics 300.

Light energy 101-T is aligned such that it is parallel to beam 502 as it impinges on beam angle adjustment mirror optics 300. It is to be understood that the term "parallel" as used herein includes the possibility that light energy 101-T and beam 502 can be coincident or collinear. Both light energy 101-T and beam 502 are adjusted in correspondence with one another by optics 300. Accordingly, light energy 101-T and beam 502 retain their parallel relationship when they are incident on eye 10. Since X-Y translation mirror optics 520 shifts the position of beam 502 in translation independently of optics 300, the parallel relationship between beam 502 and light energy 101-T is maintained throughout the particular ophthalmic procedure.

Beam angle adjustment mirror optics consists of independently rotating mirrors 310 and 320. Mirror 310 is rotatable about axis 312 as indicated by arrow 314 while mirror 320 is rotatable about axis 322 as indicated by arrow 324. Axes 312 and 322 are orthogonal to one another. In this way, mirror 310 is capable of sweeping light energy 101-T and beam 502 in a first plane (e.g., elevation) while mirror 320 is capable of independently sweeping light energy 101-T and beam 502 in a second plane (e.g., azimuth) that is perpendicular to the first plane. Upon exiting beam angle adjustment mirror optics 300, light energy 101-T and beam 502 impinge on eye 10.

Figure 4:
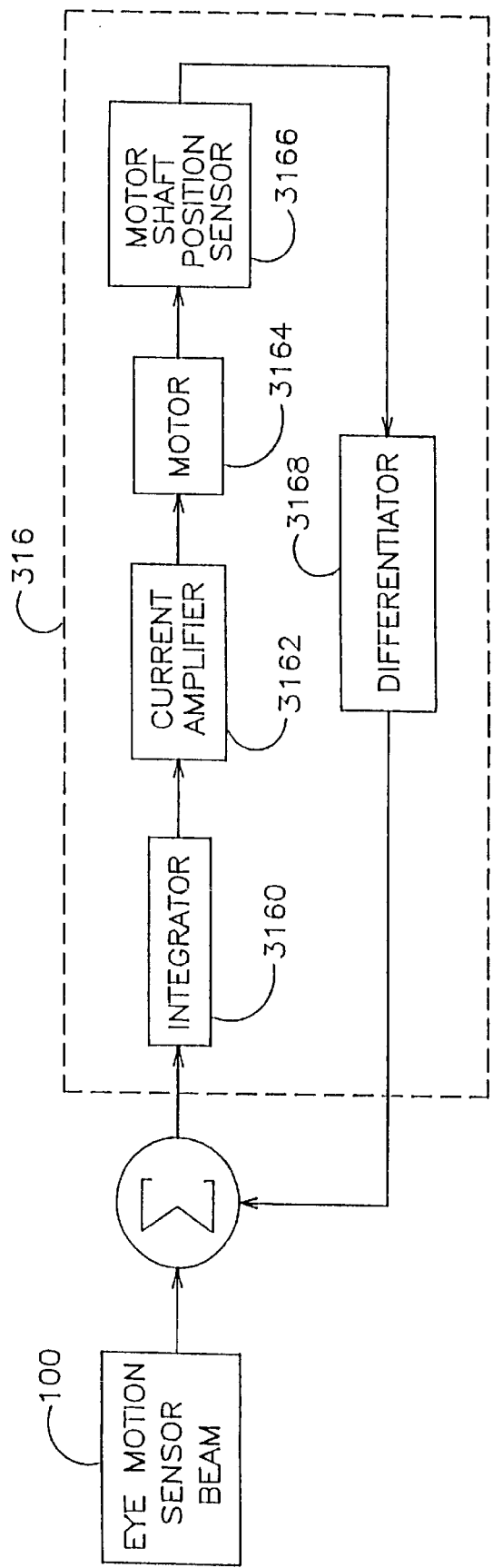
FIG. 4 is a block diagram of the servo controller/motor driver circuitry used in the ophthalmic treatment laser embodiment of the present invention.

Movement of mirrors 310 and 320 is typically accomplished with servo controller/motor drivers 316 and 326, respectively. FIG. 4 is a block diagram of a preferred embodiment servo controller/motor driver 316 used for the illustrative PRK/PTK treatment example. (The same structure is used for servo controller/motor driver 326.) In general, drivers 316 and 326 must be able to react quickly when the measured error from eye movement sensor 100 is large, and further must provide very high gain from low frequencies (DC) to about 100 radians per second to virtually eliminate both steady state and transient error.

More specifically, eye movement sensor 100 provides a measure of the error between the center of the pupil (or an offset from the center of the pupil that the doctor selected) and the location where mirror 310 is pointed. Position sensor 3166 is provided to directly measure the position of the drive shaft (not shown) of galvanometer motor 3164. The output of position sensor 3166 is differentiated at differentiator 3168 to provide the velocity of the drive shaft of motor 3164. This velocity is summed with the error from eye movement sensor 100. The sum is integrated at integrator 3160 and input to current amplifier 3162 to drive galvanometer motor 3164. As the drive shaft of motor 3164 rotates mirror 310, the error that eye movement sensor 100 measures decreases to a negligible amount. The velocity feedback via position sensor 3166 and differentiator 3168 provides servo controller/motor driver 316 with the ability to react quickly when the measured sensor error is large.

Light energy reflected from eye 10, as designated by reference numeral 101-R, travels back through optics 300 and beamsplitter 200 for detection at sensor 100. Sensor 100 determines the amount of eye movement based on the changes in reflection energy 101-R. Error control signals indicative of the amount of eye movement are fed back by sensor 100 to beam angle adjustment mirror optics 300. The error control signals govern the movement or realignment of mirrors 310 and 320 in an effort to drive the error control signals to zero. In doing this, light energy 101-T and beam 502 are moved in correspondence with eye movement while the actual position of beam 502 relative to the center of the pupil is controlled by X-Y translation mirror optics 520.

In order to take advantage of the properties of beamsplitter 200, light energy 101-T must be of a different wavelength than that of treatment laser beam 502. The light energy should preferably lie outside the visible spectrum so as not to interfere or obstruct a surgeon's view of eye 10. Further, if the present invention is to be used in ophthalmic surgical procedures, light energy 101-T must be "eye safe" as defined by the American National Standards Institute (ANSI). While a variety of light wavelengths satisfy the above requirements, by way of example, light energy 101-T is infrared light energy in the 900 nanometer wavelength region. Light in this region meets the above noted criteria and is further produced by readily available, economically affordable light sources. One such light source is a high pulse repetition rate GaAs 905 nanometer laser operating at 4 kHz which produces an ANSI defined eye safe pulse of 10 nanojoules in a 50 nanosecond pulse.

Figure 5:
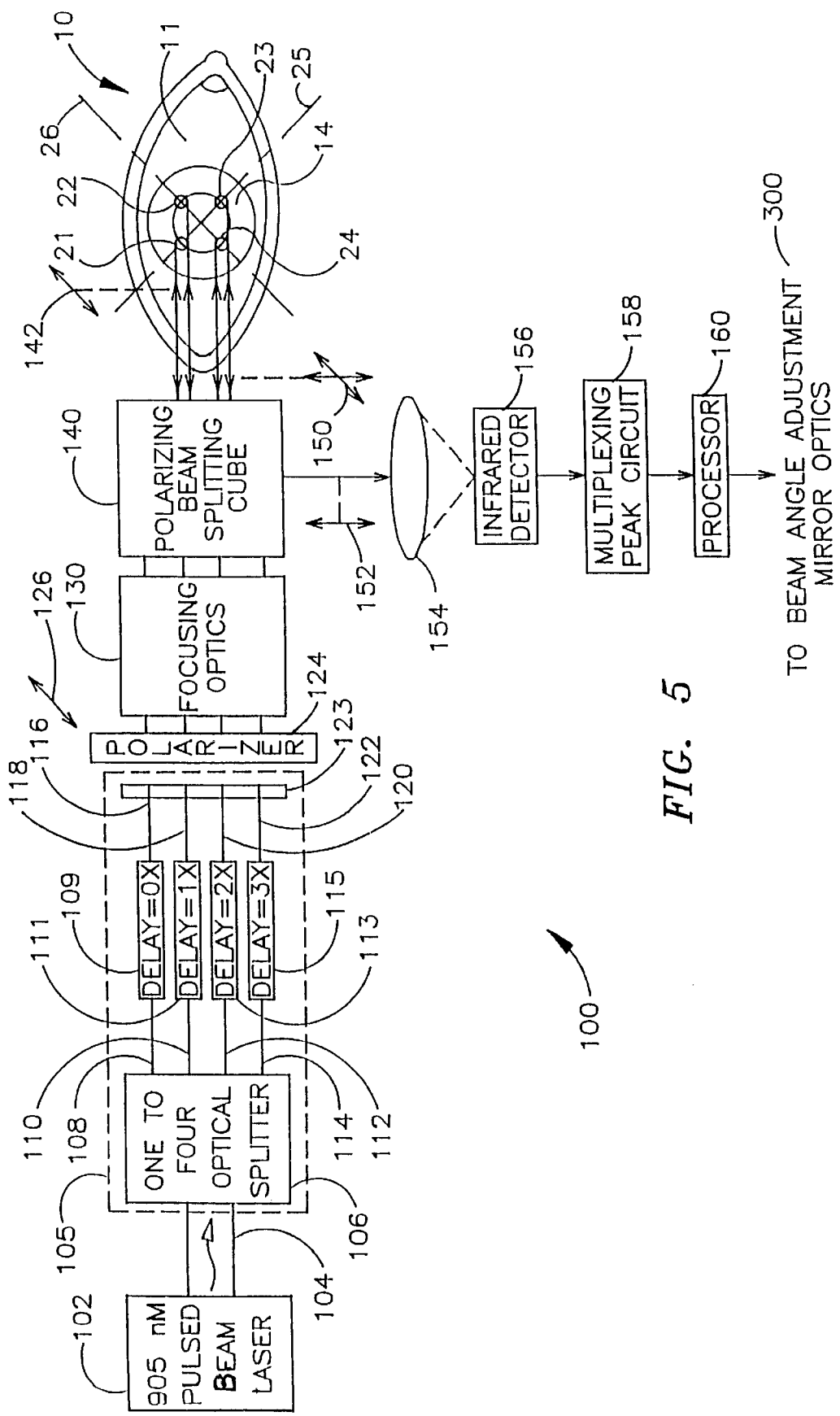
FIG. 5 is a block diagram of a preferred embodiment eye movement sensor used in the ophthalmic treatment laser embodiment of the present invention.

A preferred embodiment method for determining the amount of eye movement, as well as eye movement sensor 100 for carrying out such a method, are described in detail in the aforementioned copending patent application. However, for purpose of a complete description, sensor 100 will be described briefly with the aid of the block diagram shown in FIG. 5. Sensor 100 may be broken down into a delivery portion and a receiving portion. Essentially, the delivery portion projects light energy 101-T in the form of light spots 21, 22, 23 and 24 onto a boundary (e.g., iris/pupil boundary 14) on the surface of eye 10. The receiving portion monitors light energy 101-R in the form of reflections caused by light spots 21, 22, 23 and 24.

In delivery, spots 21 and 23 are focused and positioned on axis 25 while spots 22 and 24 are focused and positioned on axis 26 as shown. Axes 25 and 26 are orthogonal to one another. Spots 21, 22, 23 and 24 are focused to be incident on and evenly spaced about iris/pupil boundary 14. The four spots 21, 22, 23 and 24 are of equal energy and are spaced evenly about and on iris/pupil boundary 14. This placement provides for two-axis motion sensing in the following manner. Each light spot 21, 22, 23 and 24 causes a certain amount of reflection at its position on iris/pupil boundary 14. Since boundary 14 moves in coincidence with eye movement, the amount of reflection from light spots 21, 22, 23 and 24 changes in accordance with eye movement. By spacing the four spots evenly about the circular boundary geometry, horizontal or vertical eye movement is detected by changes in the amount of reflection from adjacent pairs of spots. For example, horizontal eye movement is monitored by comparing the combined reflection from light spots 21 and 24 with the combined reflection from light spots 22 and 23. In a similar fashion, vertical eye movement is monitored by comparing the combined reflection from light spots 21 and 22 with the combined reflection from light spots 23 and 24.

More specifically, the delivery portion includes a 905 nanometer pulsed diode laser 102 transmitting light through optical fiber 104 to an optical fiber assembly 105 that splits and delays each pulse from laser 102 into preferably four equal energy pulses. Assembly 105 includes one-to-four optical splitter 106 that outputs four pulses of equal energy into optical fibers 108, 110, 112, 114. In order to use a single processor to process the reflections caused by each pulse transmitted by fibers 108, 110, 112 and 114, each pulse is uniquely delayed by a respective fiber optic delay line 109, 111, 113 and 115. For example, delay line 109 causes a delay of zero, i.e., DELAY=0x where x is the delay increment; delay line 111 causes a delay of x, i.e., DELAY=1x; etc.

The pulse repetition frequency and delay increment x are chosen so that the data rate of sensor 100 is greater than the speed of the movement of interest. In terms of saccadic eye movement, the data rate of sensor 100 must be on the order of at least several hundred hertz. For example, a sensor data rate of approximately 4 kHz is achieved by 1) selecting a small but sufficient value for x to allow processor 160 to handle the data (e.g., 160 nanoseconds), and 2) selecting the time between pulses from laser 102 to be 250 microseconds (i.e., laser 102 is pulsed at a 4 kHz rate).

The four equal energy pulses exit assembly 105 via optical fibers 116, 118, 120 and 122 which are configured as a fiber optic bundle 123. Bundle 123 arranges the optical fibers such that the center of each fiber forms the corner of a square. Light from assembly 105 is passed through an optical polarizer 124 that outputs horizontally polarized light beams as indicated by arrow 126. Horizontally polarized light beams 126 pass to focusing optics 130 where spacing between beams 126 is adjusted based on the boundary of interest. Additionally, a zoom capability (not shown) can be provided to allow for adjustment of the size of the pattern formed by spots 21, 22, 23 and 24. This capability allows sensor 100 to adapt to different patients, boundaries, etc.

A polarizing beam splitting cube 140 receives horizontally polarized light beams 126 from focusing optics 130. Cube 140 is configured to transmit horizontal polarization and reflect vertical polarization. Accordingly, cube 140 transmits only horizontally polarized light beams 126 as indicated by arrow 142. Thus, it is only horizontally polarized light that is incident on eye 10 as spots 21, 22, 23 and 24. Upon reflection from eye 10, the light energy is depolarized (i.e., it has both horizontal and vertical polarization components) as indicated by crossed arrows 150.

The receiving portion first directs the vertical component of the reflected light as indicated by arrow 152. Thus, cube 140 serves to separate the transmitted light energy from the reflected light energy for accurate measurement. The vertically polarized portion of the reflection from spots 21, 22, 23 and 24, is passed through focusing lens 154 for imaging onto an infrared detector 156. Detector 156 passes its signal to a multiplexing peak detecting circuit 158 which is essentially a plurality of peak sample and hold circuits, a variety of which are well known in the art. Circuit 158 is configured to sample (and hold the peak value from) detector 156 in accordance with the pulse repetition frequency of laser 102 and the delay x. For example, if the pulse repetition frequency of laser 102 is 4 kHz, circuit 158 gathers reflections from spots 21, 22, 23 and 24 every 250 microseconds.

The values associated with the reflected energy for each group of four spots (i.e., each pulse of laser 102) are passed to a processor 160 where horizontal and vertical components of eye movement are determined. For example let $R_{21}$, $R_{22}$, $R_{23}$ and $R_{24}$ represent the detected amount of reflection from one group of spots 21, 22, 23 and 24, respectively. A quantitative amount of horizontal movement is determined directly from the normalized relationship.

$$\frac{(R_{21} + R_{24}) - (R_{22} + R_{23})}{R_{21} + R_{22} + R_{23} + R_{24}} \quad (1)$$

while a quantitative amount of vertical movement is determined directly from the normalized relationship.

$$\frac{(R_{21} + R_{22}) - (R_{23} + R_{24})}{R_{21} + R_{22} + R_{23} + R_{24}} \quad (2)$$

Note that normalizing (i.e., dividing by $R_{21}+R_{22}+R_{23}+R_{24}$) reduces the effects of variations in signal strength. Once determined, the measured amounts of eye movement are sent to beam angle adjustment mirror optics 300.

The advantages of the present invention are numerous. Eye movement is measured quantitatively and used to automatically redirect both the laser delivery and eye tracking portions of the system independent of the laser positioning mechanism. The system operates without interfering with the particular treatment laser or the surgeon performing the eye treatment procedure.

Although the invention has been described relative to a specific embodiment thereof, there are numerous variations and modifications that will be readily apparent to those skilled in the art in the light of the above teachings. It is therefore to be understood that, within the scope of the appended claims, the invention may be practiced other than as specifically described.

What is claimed as new and desired to be secured by Letters Patent of the United States is:

1. An eye tracking, targeting and laser delivery system comprising:
   at least three first laser beams that are directed toward an eye, the first laser beams each having a first beam path, the first laser beams having wavelengths that will at least partially reflect from the eye for providing reflected first laser beams having a reflected beam path;
   means for sequentially delaying the at least three first laser beams for permitting a sequential delivery to the eye; and
   a second laser beam, having a wavelength that is different than the first laser beam; the second laser beam having a second beam path; and a movable mirror positioned in the first beam path, the second beam path and the reflected beam path; the first beam path, the second beam path and the reflected beam path being parallel between the mirror and the eye.

2. The system of claim 1, further comprising a third movable mirror positioned solely in the second beam path.

3. The system of claim 2, wherein the third movable mirror is positioned solely in the second beam path.

4. The system of claim 1, further comprising a second movable mirror positioned in the first beam path, the second beam path and the reflected beam path, the paths having a parallel relationship between the movable mirror and the second movable mirror.

5. The system of claim 4, further comprising a third movable mirror positioned in the second beam path.

6. The system of claim 5, further comprising a fourth movable mirror positioned in the second beam path.

7. An eye tracking, targeting and laser delivery system comprising:
- at least three first laser beams that are directed toward an unrestrained eye, the reflected first laser beams each having a first beam path; the first beam paths being parallel; the first laser beams having a wavelength that will at least partially reflect from the eye, the first laser beams having a reflected beam path;
- means for sequentially delaying the at least three first laser beams for permitting a sequential delivery to the eye; and
- a second laser beam, having a wavelength that is different than a first laser beam; the second laser beam having a second beam path; a movable mirror positioned in the first beam path, the second beam path and the reflected beam path; the first beam path, the second beam path and the reflected beam path being parallel between the mirror and the eye.

8. The system of claim 7, wherein the first laser beams are eye safe.

9. The system of claim 7, further comprising a third movable mirror positioned in the second beam path.

10. The system of claim 9, wherein the third movable mirror is positioned solely in the second beam path.

11. The system of claim 7, further comprising a second movable mirror positioned in the first beam path, the second beam path and the reflected beam path, the paths having a parallel relationship between the movable mirror and the second movable mirror.

12. The system of claim 11, further comprising a third movable mirror positioned in the second beam path.

13. The system of claim 12, further comprising a fourth movable mirror positioned in the second beam path.

14. A laser vision correction system comprising:
- means for generating a treatment laser beam along a treatment laser path;
- means for translating the treatment laser path to provide a predetermined sequence of shots in a predetermined pattern on an eye;
- means for generating a plurality of discrete tracking laser beams along a tracking laser path;
- means for sequentially delaying the plurality of laser beams to constitute a shot sequence having a time delay with respect to each other; and
- means for shifting the treatment laser beam to follow eye movement so that the predetermined shot pattern is placed on a predetermined location on the eye.

15. The laser vision correction system of claim 14, wherein the eye movement comprises saccadic eye movement.

16. A laser vision correction system comprising:
- means for generating a treatment laser beam along a treatment laser path;
- means for translating the treatment laser path to provide a predetermined sequence of individual shots at predetermined locations on an eye;
- means for generating a plurality of discrete tracking laser beams along a tracking laser path;
- means for sequentially delaying the plurality of laser beams to constitute a shot sequence having a time delay with respect to each other; and
- means for minimizing the effect of eye movement, without restraining said movement, on the placement of the predetermined sequence of individual shots at the predetermined locations on the eye.

17. The laser vision correction system of claim 16 in which the eye movement comprises saccadic eye movement.

18. A method of delivering a treatment laser beam to an eye comprising:
- selecting a patient's eye to which a laser beam is to be delivered;
- providing four eye safe discrete tracking laser beams;
- delaying the four tracking laser beams with respect to each other to constitute a sequence of laser beams;
- directing the tracking laser beams to the eye, and reflecting the tracking laser beams from the eye;
- providing a sensor to monitor the tracking laser beams that are reflected from the eye;
- providing a treatment laser beam;
- directing the treatment laser beam to the eye;
- contacting the eye with the treatment laser beam in a series of discrete shots, the position of each shot in the series being directed to a predetermined location on the eye; and
- directing the treatment laser beam based on a signal associated with the monitoring sensor to track the motion of the eye and contact the eye at the predetermined location for each shot in the series.

19. The method of claim 18 in which the treatment laser beam is an excimer beam.

20. The method of claim 18 in which the delivered tracking laser beams, the reflected tracking laser beams, and the treatment laser beam are in a parallel relationship along a portion of their respective paths.

21. The method of claim 18 in which the series of shots is delivered to the eye in a manner in which no two sequential shots are delivered to the exact same location on the eye.

22. A method of delivering a laser beam to an eye comprising:
- providing a head support for a patient and placing the patient's head on the head support;
- selecting the patient's eye to which a laser beam is to be delivered;
- maintaining the eye free from external restraints;
- providing plurality of discrete eye safe tracking laser beams;
- delaying the plurality of tracking laser beams with respect to each other to constitute a sequence of laser beams;
- directing the tracking laser beams to the eye, and reflecting the tracking laser beams from the eye;
- providing a sensor to monitor the tracking laser beams that is reflected from the eye;
- providing a treatment laser beam;
- directing the treatment laser beam to the eye;
- contacting the eye with the treatment laser beam in a series of discrete shots, the position of each shot in the series being directed to a predetermined location on the eye; and
- directing the treatment laser beam based on a signal associated with the monitoring sensor to track the motion of the eye and contact the eye at the predetermined location for each shot in the series.

23. The method of claim 22 in which the treatment laser beam is an excimer beam.

24. The method of claim 22 in which the delivered tracking laser beams, the reflected tracking laser beams, and the treatment laser beam are in a parallel relationship along a portion of their respective paths.

25. The method of claim 23 in which the series of shots is delivered to the eye in a manner in which no two sequential shoots are delivered to the exact same location on the eye.

26. A method of minimizing the effect of saccadic eye movement on the delivery of a treatment laser to an eye comprising:
   selecting a patient's eye to which a laser beam is to be delivered;
   providing plurality of discrete eye safe tracking laser beams;
   delaying the plurality of tracking laser beams with respect to each other to constitute a sequence of laser beams;
   directing the tracking laser beams to the eye, and reflecting the tracking laser beams from the eye;
   providing a sensor to monitor the tracking laser beams that is reflected from the eye;
   providing a treatment laser;
   directing the treatment laser to the eye;
   contacting the eye with the treatment laser in a series of discrete shots, the position of each shot in the series being directed to a predetermined location on the eye;
   directing the treatment laser beam to track the saccadic motion of the eye; and
   minimizing the error caused by saccadic eye motion in contacting the eye with the treatment laser beam at a predetermined location on the eye.

27. The method of claim 26 in which the treatment laser beam is an excimer beam.

28. The method of claim 27 in which the delivered tracking laser beams, the reflected tracking laser beams, and the treatment laser beam are in a parallel relationship along a portion of there respective paths.

29. The method of claim 27 in which the series of shots is delivered to the eye in a manner in which no two sequential shots are delivered to the exact same location on the eye.

30. A method of reducing error caused by saccadic eye movement on the delivery of a treatment laser to an eye comprising:
   providing a head support for a patient and placing the patients head on the head support;
   selecting the patient's eye to which a treatment laser beam is to be delivered;
   maintaining the eye free from external restraints;
   providing plurality of discrete eye safe tracking laser beams;
   directing the tracking laser beams to the eye in sequentially time-delayed fashion, and reflecting the tracking laser beams from the eye;
   providing a sensor to monitor positions of the tracking laser beams that are reflected from the eye;
   providing a treatment laser beam;
   directing the treatment laser beam to the eye;
   contacting the eye with the treatment laser beam in a series of discrete shots, the position of each shot in the series being directed to a predetermined location on the eye; and
   reducing the error caused by saccadic eye motion in contacting the eye with the treatment laser beam at a predetermined location on the eye by using the sensed reflected tracking laser beams positions to automatically translate the position of each treatment laser beam shot commensurate with the tracking laser beams positions.

31. The method of claim 30 in which the treatment laser beam is an excimer beam.

32. The method of claim 30 in which the delivered tracking laser beams, the reflected tracking laser beams, and the treatment laser beam are in a parallel relationship along a portion of their respective paths.

33. The method of claim 30 in which the series of shots is delivered to the eye in a manner in which no two sequential shots are delivered to the exact same location on the eye.

34. A multiple laser system for tracking and performing procedures on an eye comprising.
   a tracking laser source that generates a plurality of discrete tracking laser beams along a tracking beam path;
   means for sequentially delaying the plurality of laser beams to constitute a shot sequence having a time delay with respect to each other;
   an excimer laser source that generates an excimer laser beam along an excimer beam path, the excimer laser beam having a wavelength that is different from the tracking laser beam;
   the tracking laser beam having a wavelength that will not damage the eye and that will reflect from the eye;
   a shot pattern mirror positioned in the excimer beam path and not in the tracking beam path;
   a controller operationally associated with the shot pattern mirror;
   a beam splitter positioned in the tracking laser and excimer beam paths, the beam splitter substantially reflecting the excimer laser beam and substantially transmitting the tracking laser beam, the beam splitter positioned at an angle other than 90 degrees with respect to the excimer beam path;
   a laser tracking mirror positioned in the tracking and excimer beam paths; a controller operationally associated with the laser tracking mirror;
   an eye motion sensor positioned in the system in the path of the tracking laser beam after the tracking laser beam has been reflected from the eye; and
   the laser tracking mirror and the beam splitter positioned in the path of the tracking laser beam after it has been reflected from the eye, said mirror and splitter being position in the reflected path of the tracking laser beam between the eye and the eye motion sensor.

35. The system of claim 34, wherein the plurality of tracking laser beams comprises four laser beams.

36. The system of claim 34, wherein the controller operationally associated with the shot pattern mirror further comprises a memory that stores a predetermined shot sequence for said excimer laser.

37. The system of claim 34, wherein the controller operationally associated with the shot pattern mirror provides signals to an operationally associated motor; the controller having a predetermined shot sequence for the excimer laser; and the controller being capable of controlling the associated motor to move the shot pattern mirror in said predetermined shot sequence; said sequence having no two sequential shots striking exactly the same spot on the eye; and wherein the plurality of tracking laser beams comprises three tracking laser beams; each of the tracking laser beams having a time delay with respect to the other.

38. The system of claim 34, wherein the reflected beam path, the tracking beam path and the excimer beam path are parallel over at least a portion of their respective paths.

39. An apparatus for delivering a laser beam comprising:
a first laser source that generates a plurality of discrete first laser beams along a first beam path, the first laser beams having a wavelength that is eye safe;
means for sequentially delaying the plurality of laser beams to constitute a shot sequence having a time delay with respect to each other;
a second laser source that generates a second laser beam along a second beam path, the second laser beam having a wavelength that is different from the first laser beams, the second laser beam having a wavelength suitable for cutting the eye;
a laser translation mirror positioned in the path of the second laser beam;
a motor and a controller operationally associated with the laser translation mirror;
a beam splitter positioned in the paths of the first and the second laser beams, the beam splitter being reflective to the second laser beam and being transmissive to the first laser beams;
a laser tracking mirror movably positioned in the paths of the first and second laser beams for focusing the first and the second laser beams onto an eye;
a motor and a controller associated with the laser tracking mirror;
an eye motion sensor positioned in the path of the first laser beams after they have been reflected from the eye;
the laser tracking mirror and the beam splitter positioned in the path of the first laser beams after they have been reflected from the eye, the mirror and splitter being positioned in the reflected path of the first laser beams between the eye and the eye motion sensor; and
a laser tracking mirror controller operationally associated with the eye motion sensor, wherein the eye motion sensor detects movement of the eye causing the tracking mirror to move in a manner that results in the second laser beam tracking the eye motion.

40. The apparatus of claim 39, wherein the plurality of first laser beams comprises four laser beams.

41. The apparatus of claim 39, wherein the controller operationally associated with the laser translation mirror further comprises a memory that stores a predetermined shot sequence for said second laser; and said predetermined shot sequence; having that of no two sequential shots striking the exact same spot on the eye.

42. The apparatus of claim 39, wherein the controller operationally associated with the laser translation mirror provides signals to the associated motor; said controller having a predetermined shot sequence for said second laser; and said controller being capable of controlling the associated motor to move the mirror in said predetermined shot sequence; such that no two sequential shot strike the same spot on the eye; and wherein the plurality of first laser beams comprises four first laser beams.

43. The apparatus of claim 39, wherein the reflected beam path, the first beam path and the second beam path are parallel over at least a portion of their respective paths.

44. The apparatus of claim 39, wherein the second laser beam is an excimer laser beam.

* * * * *